United States Patent
Hannemann (10) Patent No.: US 9,974,513 B2
(45) Date of Patent: May 22, 2018

(54) METHOD FOR DETERMINING THE ROTATION ANGLE OF A ROTOR-STATOR DEVICE, WITH SLIP RING ARRANGEMENT AND COMPUTER TOMOGRAPH

(71) Applicant: Siemens Healthcare GmbH, Erlangen (DE)

(72) Inventor: Thilo Hannemann, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days. days.

(21) Appl. No.: 15/703,050

(22) Filed: Sep. 13, 2017

(65) Prior Publication Data
US 2018/0085085 A1 Mar. 29, 2018

(30) Foreign Application Priority Data
Sep. 29, 2016 (DE) .................. 10 2016 218 888

(51) Int. Cl.
*A61B 6/03* (2006.01)
*A61B 6/00* (2006.01)
*H05G 1/26* (2006.01)

(52) U.S. Cl.
CPC .............. *A61B 6/56* (2013.01); *A61B 6/032* (2013.01); *H05G 1/26* (2013.01)

(58) Field of Classification Search
CPC .............. A61B 6/035; A61B 6/56; H05G 1/26
See application file for complete search history.

(56) References Cited

U.S. PATENT DOCUMENTS

| 3,225,605 A | * | 12/1965 | Slater | .................. G01P 7/00 |
| | | | | 310/105 |
| 3,365,799 A | * | 1/1968 | Fisher | .................. G01P 3/44 |
| | | | | 250/229 |
| 3,691,560 A | * | 9/1972 | Hammack | .............. G01S 1/302 |
| | | | | 342/387 |

(Continued)

FOREIGN PATENT DOCUMENTS

| DE | 102004042486 A1 | 3/2006 | |
| WO | WO 2009147569 A1 | * 12/2009 | ............. A61B 6/547 |

OTHER PUBLICATIONS

German Office Action for German Application No. 102016218888.7 dated Apr. 4, 2017 and English Translation thereof.

(Continued)

*Primary Examiner* — Thomas R Artman
(74) *Attorney, Agent, or Firm* — Harness, Dickey & Pierce, P.L.C.

(57) ABSTRACT

A method and a device are for determining the rotation angle of a rotor-stator device. The rotor-stator device has a slip ring arrangement for transferring data between rotor and stator. In an embodiment, the device includes a signal conductor, essentially ring-shaped or ring-segment-shaped, fixed to a ring-shaped support structure; a transmitter for injecting a data signal into the signal conductor; and a receiver for reading the data signal out from the signal conductor. The transmitter and receiver move in opposite directions synchronously with the rotation between rotor and stator. According to an embodiment of the method, a signal is injected into the signal conductor. The signal is used to generate a metrologically detectable characteristic from which the rotation angle is ascertained.

20 Claims, 2 Drawing Sheets

(56) References Cited

U.S. PATENT DOCUMENTS

| | | | | |
|---|---|---|---|---|
| 3,866,229 | A * | 2/1975 | Hammack | G01S 1/302 |
| | | | | 342/451 |
| 3,906,339 | A * | 9/1975 | Leisterer | G01D 5/208 |
| | | | | 324/207.18 |
| 7,126,621 | B2 * | 10/2006 | Castelli | G03G 15/0163 |
| | | | | 347/234 |
| 8,969,789 | B2 * | 3/2015 | Sato | G01D 5/24466 |
| | | | | 250/214 R |
| 9,301,384 | B2 * | 3/2016 | Zwart | H05H 7/04 |
| 9,706,636 | B2 * | 7/2017 | Zwart | H05H 7/04 |
| 2006/0024104 | A1 * | 2/2006 | Castelli | G03G 15/0163 |
| | | | | 399/372 |
| 2006/0054798 | A1 * | 3/2006 | Welker | G01D 5/3473 |
| | | | | 250/231.14 |
| 2011/0069819 | A1 * | 3/2011 | Urban | A61B 6/547 |
| | | | | 378/197 |
| 2013/0240719 | A1 * | 9/2013 | Sato | G01D 5/34 |
| | | | | 250/231.14 |
| 2014/0094639 | A1 * | 4/2014 | Zwart | H05H 7/04 |
| | | | | 600/1 |
| 2016/0205760 | A1 * | 7/2016 | Zwart | H05H 7/04 |
| | | | | 315/502 |

OTHER PUBLICATIONS

German Decision to Grant a Patent for German Application No. 102016218888.7 dated Jul. 28, 2017 and English Translation thereof.

* cited by examiner

METHOD FOR DETERMINING THE ROTATION ANGLE OF A ROTOR-STATOR DEVICE, WITH SLIP RING ARRANGEMENT AND COMPUTER TOMOGRAPH

PRIORITY STATEMENT

The present application hereby claims priority under 35 U.S.C. § 119 to German patent application number DE 102016218888.7 filed Sep. 29, 2016, the entire contents of which are hereby incorporated herein by reference.

FIELD

At least one embodiment of the invention generally relates to a method for determining the rotation angle of a rotor-stator device which comprises a slip ring arrangement for data transfer. At least one embodiment of the invention further generally relates to a slip ring arrangement which is suitable for performing the method.

BACKGROUND

A typical example of a rotor-stator device is provided by a computer tomograph (CT). A computer tomograph normally comprises a slewing ring which can be rotated relative to a stationary suspension and to which an X-ray source (X-ray tube) and a radially opposite (X-ray) detector are connected. The slewing ring rotates as instructed about an object that is to undergo X-ray examination, and the X-radiation which is emitted and modified during the X-ray examination of the object is detected by the detector. The combination of a rotating slewing ring and a stationary suspension of the slewing ring is referred to collectively as a "gantry" in the following.

A so-called slip ring arrangement is normally used to transfer measurement and control data between the rotating part and the stationary part of the gantry. The slip ring arrangement typically comprises a ring-shaped transfer element (referred to in the following as a signal conductor), which is fastened to the rotating part or to the stationary part of the gantry. The signal conductor is often segmented over its circumference, such that each signal conductor segment can provide a separate data channel. The slip ring arrangement further comprises a number of transmitters and receivers, which are used to inject data into and read data out from the signal conductor or the respective signal conductor segment.

A direct sliding contact (mechanical) or a method based on capacitive coupling is generally used as a means of transfer between transmitter/receiver and signal conductor. Optical transfer methods are likewise known.

In addition, the gantry is usually assigned an angle measuring system which is used to determine the current angular position of the rotating part of the gantry in each case. The knowledge of the current rotational position of the slewing ring is firstly required for the purpose of activating a motor which drives the slewing ring, particularly if an electronically commutated direct drive is used. The knowledge of the current angular position is also required in order to ensure the correct recording (in the case of a position-triggered system) or the correct interpretation of the recorded measurement data (in the case of a time-triggered system).

The angle measurement is usually performed using a measurement standard which is applied to the circumference of the rotating part of the gantry and is optically or inductively interpreted by a measuring head.

DE 10 2004 042 486 A1 discloses a device for measuring the angle of rotation of a rotor in relation to a stator, wherein a disk which is provided with markings can be rotated relative to a detection entity for the purpose of detecting the markings.

SUMMARY

At least one embodiment of the invention specifies a device and/or a method which allow the rotation angle of a rotor-stator device to be determined, the rotor-stator device comprising a slip ring arrangement for the transfer of data, wherein a minimum of structural space is required.

At least one embodiment of the invention is directed to a method. At least one embodiment of the invention is directed to a device. At least one embodiment of the invention is directed to a slip ring arrangement. At least one embodiment of the invention is directed to a computer tomograph. Advantageous and in some cases individually inventive embodiment variants and developments of the invention are set forth in the claims and in the following description.

At least one embodiment of the inventive method for determining the rotation angle is performed in the context of a rotor-stator device comprising a slip ring arrangement for the transfer of data between rotor and stator. The slip ring arrangement itself comprises a ring-shaped support structure, to which is fixed at least one long signal conductor, this likewise being essentially ring-shaped or ring-segment-shaped. In the case of ring-segment-shaped signal conductors, these are usually extended to form a complete ring. The slip ring arrangement further comprises at least one transmitter for injecting a data signal into the signal conductor, and at least one receiver for reading the data signal out from the signal conductor, wherein transmitter and receiver move in opposite directions synchronously with the rotation between rotor and stator.

According to at least one embodiment of the method, for the purpose of determining the rotation angle of the rotor-stator device, i.e. for the purpose of determining the current angle of rotation of the rotor relative to the stator or relative to a defined zero position, a signal is injected into the signal conductor, the signal being used to generate a metrologically detectable characteristic from which the rotation angle is ascertained.

According to at least one embodiment of the invention, the slip ring arrangement further comprises a transmit and receive unit and an evaluation unit which has a signaling link to the transmit and receive unit, the units being configured for the purpose of ascertaining the rotation angle with the aid of the method described above. In the context of at least one embodiment of the invention, the transmit and receive unit can theoretically be a transmitter and a receiver which are provided exclusively for the purpose of injecting the signal for angle measurement into the signal conductor and registering the signal for evaluation. However, the transmit and receive unit is expediently integrated into the at least one transmitter and/or the at least one receiver already provided in the slip ring arrangement.

At least one embodiment of the invention is also directed to a slip ring arrangement, the metrologically detectable characteristic generated with the aid of the signal being the signal strength on the receiver side. In order to achieve this, e.g. in the case of a capacitive decoupling of the signal, the signal conductor (in this case the "antenna structure") on the ring-shaped support structure is designed in such a way that a periodically different coupling strength is produced along the circumference. When determining the angle, the respective rotation angle is ascertained on the basis of the signal strength detected at the receiver in this case.

At least one embodiment of the invention is also directed to a computer tomograph comprising an embodiment of the slip ring arrangement.

BRIEF DESCRIPTION OF THE DRAWINGS

Example embodiments of the invention are explained in greater detail below with reference to the drawings, in which.

In all figures, corresponding parts and values are denoted by the same reference signs in each case.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the inventive method for determining the rotation angle is performed in the context of a rotor-stator device comprising a slip ring arrangement for the transfer of data between rotor and stator. The slip ring arrangement itself comprises a ring-shaped support structure, to which is fixed at least one long signal conductor, this likewise being essentially ring-shaped or ring-segment-shaped. In the case of ring-segment-shaped signal conductors, these are usually extended to form a complete ring. The slip ring arrangement further comprises at least one transmitter for injecting a data signal into the signal conductor, and at least one receiver for reading the data signal out from the signal conductor, wherein transmitter and receiver move in opposite directions synchronously with the rotation between rotor and stator.

According to at least one embodiment of the method, for the purpose of determining the rotation angle of the rotor-stator device, i.e. for the purpose of determining the current angle of rotation of the rotor relative to the stator or relative to a defined zero position, a signal is injected into the signal conductor, the signal being used to generate a metrologically detectable characteristic from which the rotation angle is ascertained.

Accordingly, in at least one embodiment of the method, the inventive slip ring arrangement for transferring data between an assigned rotor and an assigned stator comprises at least one long signal conductor which is essentially ring-shaped or ring-segment-shaped and is fixed to a ring-shaped support structure, at least one transmitter for injecting a data signal into the signal conductor, and at least one receiver for reading out the data signal from the signal conductor, wherein transmitter and receiver move in opposite directions synchronously with the rotation between rotor and stator.

In the context of embodiments of the invention, the term "signal conductor" refers to a transfer element which is configured to allow the conducted transfer of the injected signal along the slip ring arrangement or along the support structure. In the case of an electrical signal, the signal conductor is an electrical conductor accordingly. However, the invention can also be applied in principle to an optical data transfer. In this case, the signal conductor is an optical fiber accordingly.

In the context of embodiments of the invention, the injected data signal D is accordingly an electrical (or optical) signal which carries data information.

In the context of embodiments of the invention, the support structure including signal conductor can be so arranged as to be either stationary or rotatable (synchronously with the rotor). Likewise, either the transmitter is positionally fixed while the receiver is mounted in a mobile manner along a circular path, or the receiver is positionally fixed while the transmitter is mounted in a mobile manner on a circular path, such that during operation according to the slip ring arrangement either transmitter or receiver moves along a circular path synchronously with the rotation of the rotor.

According to at least one embodiment of the invention, the slip ring arrangement further comprises a transmit and receive unit and an evaluation unit which has a signaling link to the transmit and receive unit, the units being configured for the purpose of ascertaining the rotation angle with the aid of the method described above. In the context of at least one embodiment of the invention, the transmit and receive unit can theoretically be a transmitter and a receiver which are provided exclusively for the purpose of injecting the signal for angle measurement into the signal conductor and registering the signal for evaluation. However, the transmit and receive unit is expediently integrated into the at least one transmitter and/or the at least one receiver already provided in the slip ring arrangement.

At least one embodiment of the invention is based on the finding that a conventional slip ring arrangement already has many of the features required for an angle measuring system, and therefore angle information is either generated but not currently used or can be generated by way of slight modifications to the slip ring arrangement. In this case, at least one embodiment of the invention takes advantage of the fact that the signal conductor of the slip ring arrangement has a ring-shaped structure which either rotates with the rotor relative to a stationary remote terminal, or is stationary and can be sampled by a remote terminal that rotates with the rotor. At least one embodiment of the inventive synergetic utilization of the slip ring arrangement, already provided for the purpose of transferring data, as an angle measuring system advantageously means that little or no separate structural space is required for the angle measuring system. Moreover, the angle measuring system according to the invention can advantageously be realized using particularly few parts. Consequently, the manufacturing costs of the associated rotor-stator device are also minimized.

A particularly preferred embodiment variant of the invention is based on the finding that the signal injected into the signal conductor is transported via the signal conductor at a specific propagation speed. In an embodiment variant, the signal delay time of the signal between its injection point and a remote terminal is ascertained, wherein injection point and remote terminal move in opposite directions synchronously with the rotation between rotor and stator. In this way, the rotation angle is derived from the signal delay time. Since injection point and remote terminal move in opposite directions synchronously with the rotational movement of the rotor, the signal delay time is proportional to the angle of rotation formed between rotor and stator in each case. Here, the transmitter provided for transferring data is preferably selected as injection point and the receiver provided for transferring data as remote terminal.

In an advantageous embodiment variant, the fact is exploited that the injected signal is partially reflected at the receiver which is actually provided for the purpose of receiving the signal. In order to ascertain the (in this case doubled) delay time between injection point and receiver, the reflected signal portion arriving at the injection point is detected in this case and the signal delay time and/or rotation angle is ascertained therefrom. The use of the signal delay time to measure distance is known generally for testing the quality of lines (e.g. identifying a cable fault and position thereof) and is referred to as time domain reflectometry (TDR).

In a further embodiment variant, which is preferably used in the case of a slip ring arrangement for electronic data transfer, the injected signal is so generated as to form a standing wave along the signal conductor. In order to ascertain the rotation angle in this case, the amplitude of the standing wave along the signal conductor is read out, wherein the periodicity of the amplitude along the signal conductor is evaluated quasi as an "electronically generated scale" for ascertaining the rotation angle. This embodiment variant offers the simplest means of incremental angle determination, and is developed to provide absolute angle determination in particular by counting the periodicities.

In an alternative embodiment variant for realizing an absolute angle determination, provision is made for generating and evaluating at least two standing waves having different periodicities along the signal conductor. The evaluation is known in principle to a person skilled in the art, e.g. using an optical interferometer with absolute distance measurement.

The standing wave or each standing wave is preferably generated by (at least partial) reflection of the injected signal at the opposite longitudinal end of the signal conductor to the transmitter. In order to achieve this, provision is deliberately made for deviating from the usual approach, in which a termination point of the signal conductor ("antenna termination point") is realized and absorbs the injected signal.

In the case of electrical signals, the reflection of the signal can be generated in principle by a short circuit at the longitudinal end of the signal conductor or by an open end. A frequency-dependent discontinuity is preferably formed, however, such that only signals having a corresponding frequency are reflected, while a correctly terminated antenna termination point is formed for signals having a different frequency, specifically e.g. the data signal, such that the data transfer is advantageously not disrupted by the angle measurement.

In an embodiment variant of the invention which can be realized economically, the data signal that is used in any case for the purpose of transferring data between rotor and stator is used and evaluated as a signal from which the rotation angle can be determined. Use of the injected data signal for the purpose of determining the rotation angle is preferably implemented if the angle is determined as described above by way of delay time measurement, in particular time domain reflectometry.

If the angle determination is realized by forming a standing wave, the carrier signal of the data signal (onto which the data to be transferred is modulated) is expediently used for the purpose of generating the standing wave. A standing wave ratio of approximately 10% is preferably envisaged in this case, such that the angle determination advantageously has little or no effect on the data transfer.

Additionally or alternatively, a dedicated test signal (provided exclusively for angle determination) is injected into the signal conductor as a signal for determining the rotation angle. In this case, the test signal and the data signal in particular are injected into the signal conductor and evaluated in a temporally alternating manner. Alternatively, the test signal is injected at the same time as the data signal but is separated from the data signal in terms of the frequency range.

It applies generally in the context of embodiments of the invention that both the data signal to be transmitted and the optional test signal are preferably electronic high-frequency signals (HF signals).

Embodiments of the inventive method and embodiments of the inventive slip ring arrangement are preferably used in the context of a computer tomograph, specifically for the purpose of combined data transfer and angle measurement in the gantry thereof. Their use in other rotor-stator devices is however also possible.

At least one embodiment of the invention is also directed to a slip ring arrangement, the metrologically detectable characteristic generated with the aid of the signal being the signal strength on the receiver side. In order to achieve this, e.g. in the case of a capacitive decoupling of the signal, the signal conductor (in this case the "antenna structure") on the ring-shaped support structure is designed in such a way that a periodically different coupling strength is produced along the circumference. When determining the angle, the respective rotation angle is ascertained on the basis of the signal strength detected at the receiver in this case.

In a further embodiment variant, an encoding is transmitted with the aid of the signal, and the respective rotation angle is read out on the basis of the encoding. In order to achieve this, the slip ring arrangement comprises a number of ring-segment-shaped signal conductors, each signal conductor being assigned a transmitter (referred to in combination as a "transmit segment" in the following). In order to ensure an uninterrupted data transfer, the number of receivers in this case normally differs by one from the number of transmitters, (i.e. n and n+1), such that n transmitter and receiver pairs are opposite to each other at all times. By way of incorporating a transmitter identification into the data stream of the respective transmitter, the current assignment of transmitter to receiver can be determined and the rotation angle derived therefrom.

For example, if the slip ring arrangement comprises four transmit segments of 90° each, these being read out by five receivers mounted at intervals of 72°, then a change in the assignment between the transmitters and receivers occurs every 90°–72°=18°. This already makes it possible to realize an angle measuring system having 20 positions per revolution, wherein the resolution of the angle determination increases with the number n.

In a development of the embodiment variant above, a slip ring arrangement has a support structure holding at least two concentric rings, each of which is composed of ring-segment-shaped signal conductors. In particular, in order to further increase the measuring resolution, the respective rings here are divided into different numbers of signal conductors (or transmit segments). Provision is preferably made in this case for the numbers of transmitters and receivers to differ by a number other than one (e.g. by two).

Expediently, the angle determination based on the transmitter identification serves to determine the rotation angle approximately, and this is refined by angle determination within a signal conductor or transmit segment. In this case, it is advantageous that an angle determination is produced for each receiver within its currently assigned transmit segment, giving a plurality of precise determinations. This plurality of measurements can advantageously be used to improve the accuracy or operational reliability.

Figure 1:
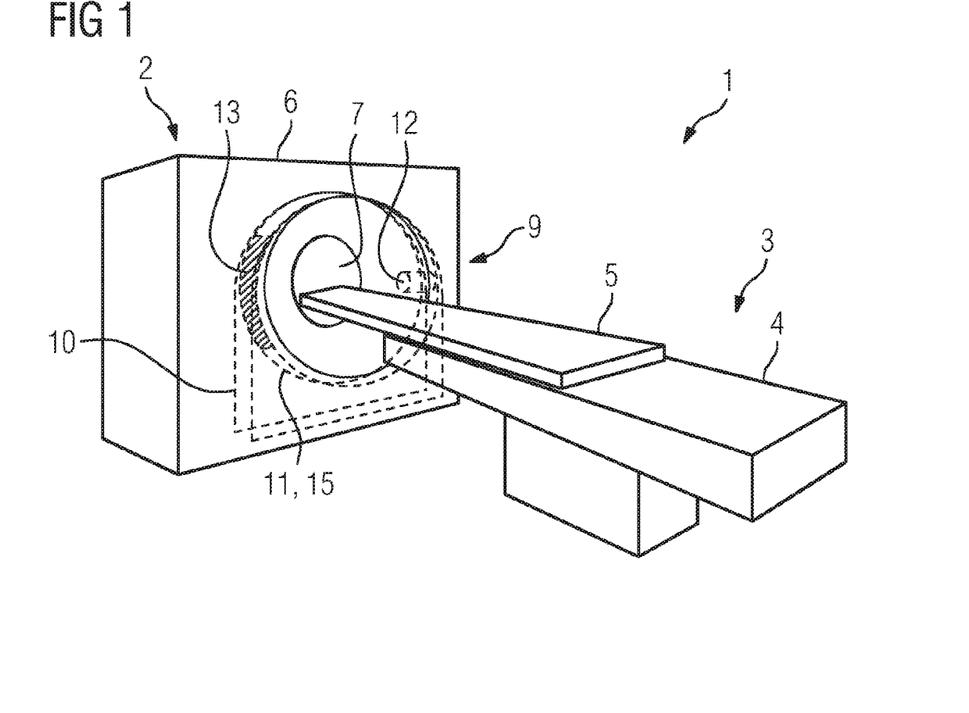
FIG. 1 shows a schematic illustration of a CT system comprising a CT device with a rotatable slewing ring and a gantry comprising a stationary suspension, with a slip ring arrangement for transferring data between slewing ring and suspension.

FIG. 1 shows a schematic illustration of a computer tomography system (CT system 1) comprising a computer tomograph (CT device 2) and a patient table 3.

The patient table 3 comprises a foot 4 which is positionally fixed and a patient couch 5 which can be moved longitudinally relative to the foot and is provided for the purpose of supporting a patient to be examined (an examination object generally).

The CT device 2 comprises a housing 6 which has a tunnel-type opening 7. A gantry 9 is contained within the housing 6.

The gantry 9 comprises a slewing ring 11 (rotor), which is rotatably mounted relative to a positionally fixed suspension 10 (stator), and to which are fastened an X-ray tube 12 and essentially radially opposite thereto an (X-ray) detector 13 for detecting X-radiation.

In order to supply the data that is recorded via the detector 13 to an evaluation computer for the purpose of evaluation, the evaluation computer typically being arranged outside the slewing ring 11 (and hence stationary), and also to transmit control data to e.g. the X-ray tube 12, a slip ring arrangement 15 is provided for bidirectional data transfer and comprises a ring-shaped support 20 (FIG. 2) which is arranged concentrically relative to the slewing ring 11.

Figure 2:
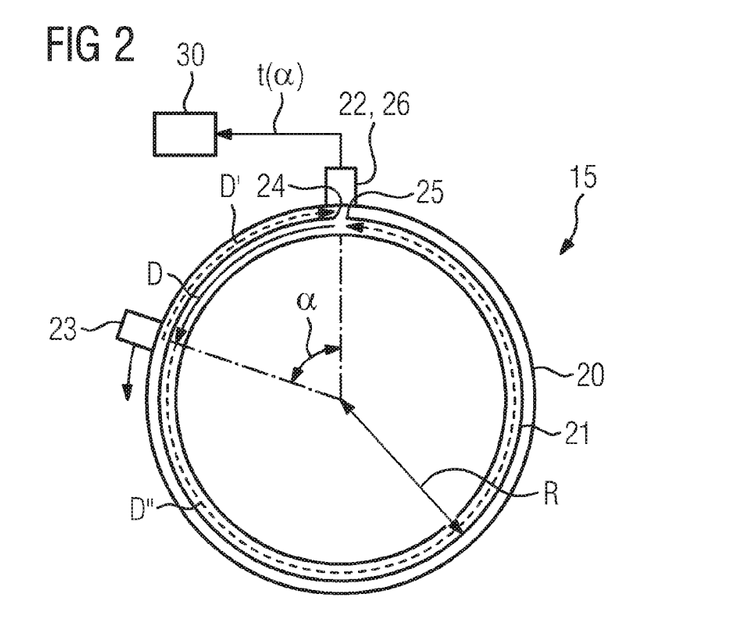
FIG. 2 shows a roughly schematic illustration of the slip ring arrangement as per FIG. 1 in accordance with a first embodiment variant.

The slip ring arrangement 15 is shown in detail in FIG. 2 in accordance with a first embodiment variant. In the embodiment variant illustrated, the support 20 is mounted in a stationary manner on the suspension 10 of the gantry 9. The slip ring arrangement 15 comprises an elongated antenna structure 21 (likewise ring-shaped and encompassing the rotor) which is fastened to the support 20, a transmitter 22 which is positionally fixed relative to the support 20 in the embodiment variant illustrated, and a receiver 23 which is arranged in a mobile manner along the circumference of the support 20 and follows the rotational movement of the slewing ring 11 (indicated by an arrow).

Although the slip ring arrangement 15 is actually configured to allow bidirectional data transfer, only the data transfer from the stator to the rotor is illustrated here for explanatory purposes.

The antenna structure 21 serves as a signal conductor, in order to carry a data signal D injected by the transmitter 22 to the receiver 23. The antenna structure 21 takes the form of an elongated electrical conductor which is installed on the support 20 on an almost closed circular path having the radius R. The first longitudinal end 24 of the conductor is connected to the transmitter 22 for the purpose of transferring signals, while the second longitudinal end 25 is arranged at a small distance from the first longitudinal end 24. The receiver 23 is configured for capacitive decoupling of the data signal D. Such a slip ring arrangement is known in principle to a person skilled in the art.

Unlike a conventional slip ring arrangement, however, a transmit and receive unit which is connected for signaling purposes to an evaluation unit 30 is formed in this case by integrating a receive unit 26 into the transmitter 22. The evaluation unit 30 is so configured as to determine, via the transmit and receive unit, the rotation angle α of the gantry 9 or more precisely of the slewing ring 11. In this case, the angle of rotation of the slewing ring 11 relative to a defined zero position is defined as the rotation angle α. Differing from the schematic illustration, the evaluation unit 30 can be integrated into the transmit and receive unit, or the receive unit 26 and the transmitter 22 can be separate structural units.

The determination of the angle is performed here essentially by way of a "time-of-flight" method, in which the delay time of the data signal D along the antenna structure 21 is evaluated in order to determine the position of the receiver 23 relative to the transmitter 22.

During operation of the slip ring arrangement 15, a data signal D in the form of a high-frequency signal (HF signal) is injected into the signal conductor 21 by the transmitter 22, and contains e.g. control data for the X-ray tube 12. A discontinuity is generated locally in the antenna structure 21 by the receiver 23, such that part of the data signal D is reflected at the receiver 23 and travels back to the transmitter 22 as reflected data signal D. The continuing part of the data signal D" is absorbed at the termination point which is formed at the longitudinal end 25 of the antenna structure 21.

The reflected portion of the data signal D' is registered by the receive unit 26. The evaluation unit 30 determines at least indirectly the signal delay time t(α), dependent on the rotation angle α, which elapsed between emission of the data signal D and receipt of the reflected portion D. The signal delay time t(α) is determined e.g. by way of cross correlation.

When ascertaining the signal delay time t(α), it is advantageous that the data transfer rate is normally many times higher than the rotational speed of the slewing ring 11. The data transfer rate lies in a range of e.g. 4-6 gigabits per second, while the rotational speed is approximately 3 revolutions per second. A precise determination can therefore be achieved by way of averaging.

The evaluation unit 30 then calculates the current rotation angle α on the basis of EQU 1:

$$\alpha = \frac{t \cdot c_S}{2 \cdot R} \quad \text{EQU 1}$$

where
  t ascertained signal delay time,
  $c_S$ propagation speed of the data signal D on the antenna structure (e.g. ⅔ of the speed of light),
  R radius of the antenna structure 21.

The rotation angle α is then supplied to the evaluation computer and/or a rotary drive of the gantry 9.

In an alternative embodiment variant, the evaluation unit 30 triggers the transmitter 22 to briefly interrupt the injection of the data signal D and to inject a measuring pulse into the antenna structure 21, the reflection of the pulse being evaluated via the receive unit 26 or the evaluation unit 30 for the purpose of angle determination.

In a further embodiment variant (not explicitly illustrated), in response to the received pulse, the receiver 23 emits a signal which is registered by the receive unit 26.

Figure 3:
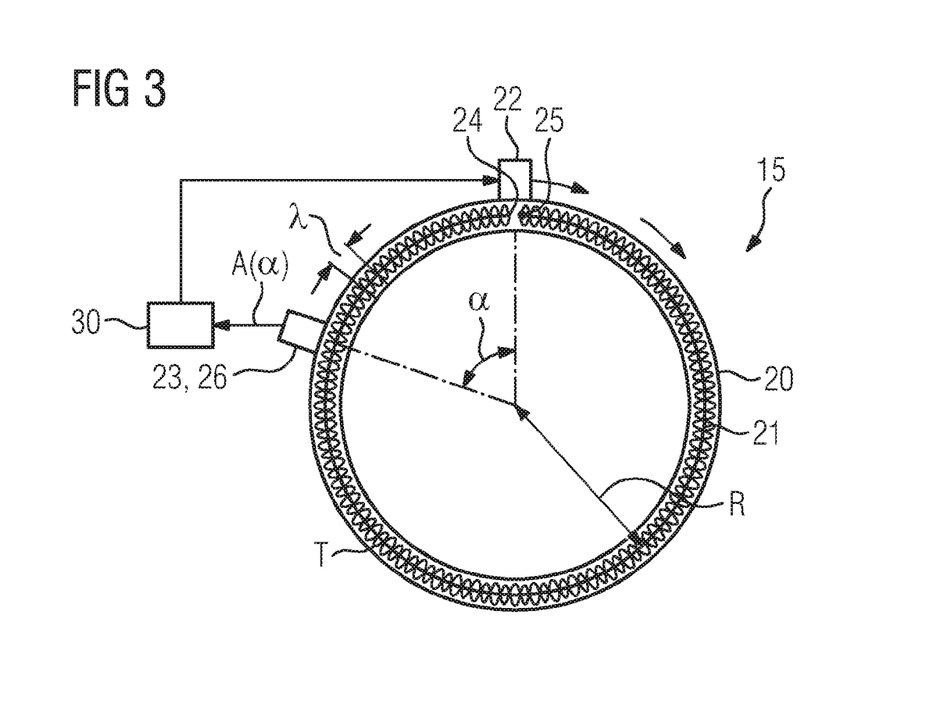
FIG. 3 shows an illustration of the slip ring arrangement as per FIG. 2 in accordance with a second embodiment variant.

FIG. 3 shows an alternative embodiment variant of the slip ring arrangement 15, which is constructed in essentially the same way as the embodiment variant described above. It does however differ in that e.g. the support 20 and the transmitter 22 attached thereto is rotatably mounted and turns with the slewing ring 11 (indicated by an arrow in each case), while the receiver 23 is so arranged as to be stationary. The receive unit 26 provided for angle measurement is assigned to the receiver 23 here, wherein transmitter 22 and receive unit 26 then form the transmit and receive unit that is provided for determining the angle.

In this embodiment variant, the determination of the rotation angle α is realized by generating a standing wave.

For example (and essentially for explanatory purposes), the antenna structure 21 is short circuited at the longitudinal end 25 in order to achieve this.

During operation of the slip ring arrangement 15, the evaluation unit 30 causes the transmitter 22 to inject a high-frequency test signal T having a frequency of e.g. 10 gigahertz (GHz) into the antenna structure 21. Since the antenna structure 21 is short circuited at the longitudinal end 25, a standing wave having the wavelength λ forms on the antenna structure 21. Alternatively, the antenna structure 21 is open for generating a standing wave at the longitudinal end 25.

The receive unit 26 is so configured as to detect the amplitude A(α) of the standing wave, wherein depending on the rotation angle α a modulation of the amplitude A(α) is produced as a result of the relative movement between receive unit 26 and antenna structure 21. The amplitude modulation can be mathematically described by EQU 2:

$$A(\alpha) = A_{max} \cdot \left| \sin\left(\frac{2 \cdot \pi \cdot \alpha \cdot R}{\lambda}\right) \right| \quad \text{EQU 2}$$

where
  A amplitude,
  $A_{max}$ maximum value of the amplitude,
  α rotation angle,
  λ wavelength of the standing wave,
  R radius of the antenna structure.

The numerical value of the sinus function is derived from the rectification for determining the amplitude in this case.

In other words, the standing wave provides a scale for the antenna structure 21, wherein a periodicity corresponding to a half-wavelength λ occurs along the antenna structure 21.

For example, a standing wave having a frequency of 10 GHz generates a periodic structure of approximately 1 cm (in the case of a propagation speed of ⅔ of the speed of light on the antenna structure 21).

If the antenna structure 21 has a circumference of 5 m, for example, there will be 500 periodicities per revolution, which can then be interpolated for greater precision as they are approximately sinusoidal.

The receive unit 26 supplies the registered amplitude A(α) to the evaluation unit 30 which, in the simplest embodiment variant, applies EQU 2 to derive an incremental angular position therefrom. (The rotational direction of the slewing ring is generally known in the case of a CT device, and therefore this is possible.) In an alternative embodiment variant, the evaluation unit 30 ascertains the absolute rotation angle α with the aid of a reference signal which indicates a zero position of the rotation. The reference signal is provided e.g. by way of an index pulse (pulse which occurs once per revolution and marks an absolute angular position, e.g. 0° here), which is generated externally using a conventional method (switch, photoelectric barrier, inductive sensor).

In a further embodiment variant (not explicitly illustrated), signals having different frequencies are used, a standing wave being generated for each of the frequencies. The receive unit 26 evaluates the respectively assigned amplitudes independently of each other (e.g. via a frequency separating filter). Since the standing waves are marked by different wavelengths due to the different frequencies, it is also possible to determine the absolute rotation angle α by comparing the amplitudes of the different signals. In order to achieve this, the wave nodes of the different standing waves must only coincide at a maximum of one point on the antenna structure 21, such that a unique positional assignment is produced from the ratio of the different amplitudes.

If the electrical signal for generating the standing wave as described above is generated as test signal T specifically for this purpose and injected at the same time as the data signal D, then a frequency which in particular is outside of the frequency range used for the data transfer is selected for the test signal T. As an alternative to the short circuit described above, the antenna termination point at the longitudinal end 25 is developed as a frequency-dependent discontinuity in this case, in particular via a series arrangement of a capacitor and an inductance. As a result, the test signal T forms a standing wave while a correctly terminated antenna structure 21 is provided for the data signal D, such that the data signal D is absorbed at the longitudinal end 25 (cf. FIG. 2). In this case, the data signal D has a frequency of 1 GHz, for example, while the frequency of the test signal T is 10 GHz.

In an alternative embodiment variant (similar to the embodiment variant according to FIG. 2), the data signal D that is used for the data transfer is also used for the purpose of determining the angle. In this case, the data signal D which is transferred from the transmitter 22 to the receiver 23 contains, for example, the image data or associated raw data recorded via the detector 13.

In this type of configuration, the data signal D includes a carrier signal (with a specific carrier frequency) onto which the data is modulated. Since the angle measurement requires a very narrow bandwidth in comparison with the data transfer (e.g. <1 MHz (megahertz) for the angle measurement compared with >1 GHz for the data transfer) the modulated data can easily be filtered out so that it does not interfere with the angle measurement.

The angle measurement only requires a small standing wave ratio, i.e. the modulation of the signal strength by the standing wave need only amount to 10%, for example, and therefore the data transfer is not disrupted. The antenna termination point at the longitudinal end 25 is deliberately so embodied as to be "less than perfect", such that the carrier signal is partly reflected. Unlike the illustration in FIG. 3, the amplitude of the standing wave then has a value other than zero at the node points.

The subject matter of the invention is not restricted to the example embodiments described in the foregoing. Rather, further embodiment variants of the invention can be derived from the foregoing description by a person skilled in the art. In particular, the methods described in the foregoing for angle determination can also be applied to slip ring arrangements having segmented antenna structures (signal conductors).

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a rotation angle of a rotor-stator device including a slip ring arrangement for transferring data between a rotor and a stator of the rotor-stator device, the slip ring arrangement including a long signal conductor, essentially ring-shaped or ring-segment-shaped, fixed to a ring-shaped support structure; a transmitter; and a receiver, the transmitter and the receiver being configured to move in opposite directions synchronously with rotation between the rotor and the stator, the method comprising:
   injecting a signal into the signal conductor via the transmitter;
   generating a metrologically detectable characteristic using the injected signal; and
   determining the rotation angle from the generated metrologically detectable characteristic, wherein the signal is so generated as to form a standing wave along the signal conductor, wherein the determining of the rotation angle includes a periodicity of an amplitude along the signal conductor as a measure for determining the rotation angle and wherein at least two standing waves having different periodicities are generated and evaluated in determining the rotation angle absolutely.

2. The method of claim 1, further comprising:
   determining a signal delay time of the signal between an injection point and a remote terminal, the injection point and the remote terminal being configured to move in opposite directions to each other synchronously with the rotation between rotor and stator, the determining including determining the rotation angle using the signal delay time.

3. The method of claim 1, wherein the injected signal is at least partly reflected at the receiver, and wherein the determining of the rotation angle includes time domain reflectometry based upon a reflected signal portion received at a point where the signal is injected.

4. The method of claim 2, wherein the signal is so generated as to form a standing wave along the signal conductor, and wherein the determining of the rotation angle includes a periodicity of an amplitude along the signal conductor as a measure for determining the rotation angle.

5. The method as claimed in claim 4, wherein the standing wave is generated by reflection of the signal at a longitudinal end of the signal conductor, which is opposite to the transmitter.

6. The method of claim 2, wherein a data signal, used for transferring data between rotor and stator, is used as a signal in the determining of the rotation angle.

7. The method of claim 2, wherein a dedicated test signal is injected into the signal conductor as the signal in the determining the rotation angle.

8. The method of claim 2, wherein the injected signal is at least partly reflected at the receiver, and wherein the determining of the rotation angle includes time domain reflectometry based upon a reflected signal portion received at the injection point.

9. The method as claimed in claim 1, wherein the standing wave is generated by reflection of the signal at a longitudinal end of the signal conductor, which is opposite to the transmitter.

10. The method of claim 1, wherein a data signal, used for transferring data between rotor and stator, is used as a signal in the determining of the rotation angle.

11. The method of claim 10, wherein a standing wave is generated from a carrier signal of the data signal.

12. The method of claim 1, wherein the standing wave is generated from a carrier signal of a data signal, used for transferring data between rotor and stator.

13. The method of claim 1, wherein, in the injecting, a dedicated test signal is injected into the signal conductor and is used as a signal in the determining the rotation angle.

14. A method for determining a rotation angle of a rotor-stator device including a slip ring arrangement for transferring data between a rotor and a stator of the rotor-stator device, the slip ring arrangement including a long signal conductor, essentially ring-shaped or ring-segment-shaped, fixed to a ring-shaped support structure; a transmitter; and a receiver, the transmitter and the receiver being configured to move in opposite directions synchronously with rotation between the rotor and the stator, the method comprising:

injecting a signal into the signal conductor via the transmitter;

generating a metrologically detectable characteristic using the injected signal; and determining the rotation angle from the generated metrologically detectable characteristic, wherein, in the injecting, a dedicated test signal is injected into the signal conductor and is used as a signal in the determining the rotation angle and wherein, in the injecting, the test signal and a data signal, used for transferring data between rotor and stator, are injected into the signal conductor in a temporally alternating manner.

15. The method of claim 14, wherein the signal is so generated as to form a standing wave along the signal conductor, and wherein the determining of the rotation angle includes a periodicity of an amplitude along the signal conductor as a measure for determining the rotation angle.

16. A slip ring arrangement for transferring data between a rotor and a stator of a rotor-stator device, comprising:

a signal conductor, essentially ring-shaped or ring-segment-shaped, fixed to a ring-shaped support structure;

a transmitter to inject a data signal and a dedicated test signal, usable for transferring data between rotor and stator, into the signal conductor in a temporally alternating manner;

a receiver to read at least one of the data signal and dedicated test signal out from the signal conductor, the transmitter and receiver being movable in opposite directions, synchronously, with rotation between the rotor and the stator; and an evaluation unit, linked to the transmitter and receiver, configured as to generate a metrologically detectable characteristic using at least one of the injected dedicated test signal and the injected data signal and to determine a rotation angle of the rotor-stator device from the generated metrologically detectable characteristic.

17. A computer tomograph comprising the slip ring arrangement of claim 16.

18. A method for determining a rotation angle of a rotor-stator device including a slip ring arrangement for transferring data between a rotor and a stator of the rotor-stator device, the slip ring arrangement including a long signal conductor, essentially ring-shaped or ring-segment-shaped, fixed to a ring-shaped support structure; a transmitter; and a receiver, the transmitter and the receiver being configured to move in opposite directions synchronously with rotation between the rotor and the stator, the method comprising:

injecting a signal into the signal conductor via the transmitter;

generating a metrologically detectable characteristic using the injected signal; and determining the rotation angle from the generated metrologically detectable characteristic, wherein the signal is so generated as to form a standing wave along the signal conductor, wherein the determining of the rotation angle includes a periodicity of an amplitude along the signal conductor as a measure for determining the rotation angle, wherein the standing wave is generated by reflection of the signal at a longitudinal end of the signal conductor, which is opposite to the transmitter and wherein at least two standing waves having different periodicities are generated and evaluated in determining the rotation angle absolutely.

19. The method of claim 18, wherein at least two standing waves having different periodicities are generated and evaluated in determining the rotation angle absolutely.

20. The method as claimed in claim 18, wherein the standing wave is generated by reflection of the signal at a longitudinal end of the signal conductor, which is opposite to the transmitter.

* * * * *